United States Patent [19]
Greenberg et al.

[11] Patent Number: 5,747,292
[45] Date of Patent: May 5, 1998

[54] CHIMERIC CYTOKINE RECEPTORS IN LYMPHOCYTES

[75] Inventors: Philip D. Greenberg, Mercer Island; Brad H. Nelson, Seattle, both of Wash.

[73] Assignee: Fred Hutchinson Cancer Research Center, Seattle, Wash.

[21] Appl. No.: 244,468

[22] PCT Filed: Apr. 6, 1994

[86] PCT No.: PCT/US94/03769
§ 371 Date: May 31, 1994
§ 102(e) Date: May 31, 1994

[87] PCT Pub. No.: WO94/22914
PCT Pub. Date: Oct. 13, 1994

Related U.S. Application Data

[63] Continuation-in-part of Ser. No. 43,389, filed as PCT/US94/03769, Apr. 6, 1994, published as WO94/22914, Oct. 13, 1994, abandoned.

[51] Int. Cl.$^6$ .................. C07K 14/715; C07K 19/00; C12N 15/62
[52] U.S. Cl. .................. 435/69.7; 435/252.3; 435/320.1; 530/350; 536/23.4
[58] Field of Search .................. 435/69.7, 252.3, 435/320.1; 530/350; 536/23.4

[56] References Cited

U.S. PATENT DOCUMENTS 5,030,576  7/1991  Dull et al. .................. 435/69.7

FOREIGN PATENT DOCUMENTS

WO 92/05794  4/1992  WIPO.

OTHER PUBLICATIONS

Hatakeyama et al., "Transmembrane signaling of interleukin 2 receptor" *J. Exp. Med.* (1987) 166:362–375.

Roussel et al., "Antibody–induced mitogenicity mediated by a chimeric CD2–c–fms receptor" *Mol. Cell. Biol.* (1990) 10:2407–2412.

Greenberg, P.D., "Adoptive T cell therapy of tumors: mechanisms operative in the recognition and elimination of tumor cells" *Advances in Immunology*, Academic Press, Inc., (1991) pp. 280–355.

Zinkernagel et al., "MHC–restricted cytotoxic T cells: studies on the biological role of polymorphic major transplantation antigens determining T–cell restriction–specificity, function, and responsiveness" *Advances in Immunology*, Academic Press, Inc., (1979) pp. 51–177.

Jacobson et al., "Measles virus–specific T4+ human cytotoxic T cell clones are restricted by class II HLA antigens" *J. Immunol.* (1984) 132(2):754–757.

Gillis et al., "Long term culture of tumour–specific cytotoxic T cells" *Nature* (1977) 268:154–156.

Cheever et al., "Augmentation of the anti–tumor therapeutic efficacy of long–term cultured T lymphocytes by in vivo administration of purified interleukin 2" *J. Exp. Med.* (1977) 155:968–980.

Reddehase et al., "CD8–positive T lymphocytes specific for murine cytomegalovirus immediate–early antigens mediate protective immunity" *J. Virology* (1987) 61(10):3102–3108.

Alderson et al. "Interleukin 7 enhances cytolytic T lymphocyte generation and induces lymphokine–activated killer cells from human peripheral blood" *J. Exp. Med.* (1990) 172:577–587.

Rosenberg et al., "Use of tumor–infiltrating lymphocytes and interleukin–2 in the immunotherapy of patients with metastatic melanoma" *New Engl. J. Med.* (1988) 319:1676–1680.

Walker et al., "HIV–specific cytotoxic T lymphocytes in seropositive individuals" *Nature* (1987) 328:345–348.

Plata et al., "AIDS virus–specific cytotoxic T lymphocytes in drug disorders" *Nature* (1987) 328:348–351.

Siliciano et al., "Analysis of host–virus interactions in AIDS with anti–gp120 T cell clones: effect of HIV sequence variation and a mechanism for CD4+ cell depletion" *Cell* (1988) 54:561–575.

Chenciner et al., "Multiple subsets of HIV–specific cytotoxic T lymphocytes in humans and in mice" *Eur. J. Immunol.* (1989) 19:1573–1544.

Walker et al., "Long–term culture and fine specificity of human cytotoxic T–lymphocyte clones reactive with human immunodeficiency virus type 1" *Proc. Natl. Acad. Sci. USA* (1989) 86:9514–9518.

Klarnet et al., "Helper–independent CD8+ cytotoxic T lymphocytes express IL–1 receptors and require IL–1 for secretion of IL–2" *J. Immunol.*(1989) 142(7):2187–2191.

Sprent et al. "Properties of purified T cell subsets" *J. Exp. Med.* (1985) 162:2068–2088.

Andrus et al., "Cytotoxic T cells both produce and respond to interleukin 2" *J. Exp. Med.* (1984) 59:647–652.

Klarnet et al., "Antigen–driven T cell clones can proliferate in vivo, eradicate disseminated leukemia, and provide specific immunologic memory" *J. Immunol.* (1987) 138(11):4012–4017.

Bernard et al., "High–affinity interleukin 2 binding by an oncogenic hybrid interleukin 2–epidermal growth factor receptor molecule" *Proc. Natl. Acad. Sci. USA* (1987) 84:2125–2129.

Takeshita et al., "Cloning of the γ chain of the humal IL–2 receptor" *Science* (1992) 257:379–382.

(List continued on next page.)

*Primary Examiner*—John Ulm
*Attorney, Agent, or Firm*—Morrison & Foerster LLP

[57] ABSTRACT

Recombinant polynucleotides are provided that encode chimeric cytokine receptors. The chimeric receptor is comprised of an extracellular domain derived from cytokine receptor A-R that binds cytokine A, used to a transmembrane and cytoplasmic domain derived from cytokine receptor B-R that binds cytokine B. When the chimeric receptor is expressed in a lymphocyte it lessens the growth dependency of the lymphocyte on cytokine B in the presence of cytokine A.

42 Claims, 6 Drawing Sheets

OTHER PUBLICATIONS

Minamoto et al., "Characterization of the heterodimeric complex of human IL–2 receptor α–β chains reconstituted in a mouse fibroblast cell line, L929" *J. Immunol.* (1990) 45(7):2177–2182.

von Boehmer et al., "LYT–2–T cell–independent functions of LYT–2⁺ cells stimulated with antigen or concanavalin A" *H. Immunol.* (1984) 133(1):59–64.

Mizuochi et al., "Role of Lymphokine–secreting CD8⁺ T cells in cytotixic T lymphocyte responses against vaccinia virus" *J. Imnmunol.* (1989) 142:270–273.

Izuhara et al., "The chimeric receptor between interleukin–2 receptor β chain and interleukin–4 receptor transduces interleukin–2 signal" *Biochemical and Biophysical Research Communications* (1993) 190:992–1000.

Boshart et al., "A very strong enhancer is located upstream of an immediate early gene of human cytomegalovirus" *Cell* (1985) 41:521–530.

Fujita et al., "Regulation of Human Interleukin–2 gene: functional DNA sequences in the 5' flanking region for the gene expression in activated T lymphocytes" *Cell* (1986) 46:401–407.

Ciccarone et al., "Identification of enhancer–like elements in human IFN–$_\tau$ genomic DNA" *Journal of Immunology* (1990) 144:725–730.

Shoemaker et al., "Transcriptional regulation of interleukin 3 gene expression in T lymphocytes" *Proc. Natl. Acad. Sci. USA* (1990) 87:9650–9654.

Manning et al., "Genomic structure and alternate splicing of 519, a gene expressed late after T cell activation" *J. Immunol.* (1992) 148(12):4036–4042.

Haddad et al., "Structural organization of the hCTLA–1 gene encoding human granzyme B" *Gene* (1990) 87:265–271.

Harper et al., "CTLA–4 and CD28 activated lymphocyte molecules are closely related in both mouse and human as to sequence, message expression, gene structure, and chromosomal location" *J. Immunol.* (1991) 147(3):1037–1044.

Heusel et al., "Structure and expression of a cluster of human hematopoietic serine protease genes found on chromosone 14q11.2" *J. Biol. Chem.* (1991).

Haddas et al., "Structure and evolutionary origin of the human granzyme H gene" *International Immunology* (1990) 3(1):57–66.

Male et al., *Advanced Immunology* (1987) Gower Publishing, London, Chapter 7, entitled "Lymphocyte and phagocyte development." pp. 7.1–7.16.

Lutzova et al., Eds., *Interleukin–2 and Killer Cells in Cancer* (1990) CRC Press, Florida, Chapter 14, by Klarnet et al., entitled "Adoptive transfer of T cells for therapy of disseminated leukemia: antigen specificity and function of tumor–reactive T cells" pp. 199–217.

Lowenthal et al., "Expression of interleukin 1 receptors is restricted to the L3T4⁺ subset of mature T lymphocytes" *J. Immunol.* (1987) 138(1):1–3.

Mori et al., "Signal transduction by interleukin 2 receptor beta chain: importance of the structural integrity as revealed by side–directed mutagenesis and generation of chimeric receptors" *Intl. Immunol.* (1990) 3:149–156.

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1:

GCCGAGCCAC GGAATGTGGG CCTGGATTTG       30

( 2 ) INFORMATION FOR SEQ ID NO:2:

( i ) SEQUENCE CHARACTERISTICS:
      ( A ) LENGTH: 26 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2:

CCGTTGACCC CACTCTGTGG AAGTGC  26

( 2 ) INFORMATION FOR SEQ ID NO:3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CCGGATCCGG CTACAGGACC CTGGGG  26

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CCGAGCACCA GCAGTGG  17

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

TGCAAACAGG AAAGGGTGGG CCTGGATTTG  30

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CAAATCCAGG CCCACCCTTT CCTGTTTGCA  30

( 2 ) INFORMATION FOR SEQ ID NO:7:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

CCGGATCCGG GGTTCAGGTT TCAGGC  26

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GCCGAGCCAC GGAATCGACT CGGTGTCCCA  30

( 2 ) INFORMATION FOR SEQ ID NO:9:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:9:

TGGGACACCG AGTCGATTCC GTGGCTCGGC                30

( 2 ) INFORMATION FOR SEQ ID NO:10:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:10:

TGCAAACAGG AAAGGCCCGT CGTCAGAACC                30

( 2 ) INFORMATION FOR SEQ ID NO:11:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:11:

GGTTCTGACG ACGGGCCTTT CCTGTTTGCA                30

CHIMERIC CYTOKINE RECEPTORS IN LYMPHOCYTES

CROSS-REFERENCE TO RELATED APPLICATIONS

This application is the national phase of international application PCT/US94/03769, filed Apr. 6, 1994, published as WO94/22914, Oct. 13, 1994 which is a continuation-in-part of U.S. Ser. No. 08/043,389, filed Apr. 6, 1993, now abandoned.

STATEMENT OF RIGHTS TO INVENTIONS MADE UNDER FEDERALLY SPONSORED RESEARCH

This invention was made in part during work supported by a grant from the National Institutes of Health (CA33084). The government has certain rights in this invention.

TECHNICAL FIELD

The invention relates to the field of immunotherapy, more specifically to the introduction of genetic material encoding chimeric cytokine receptors into lymphocytes to reduce the dependency of the activated lymphocytes on T helper cells and/or growth factors supplied by $T_H$-cells.

BACKGROUND

T lymphocytes are responsible primarily for protection against intracellular pathogens and malignant tumors. Individuals who are grossly deficient in T-cell immunity frequently succumb to overwhelming infections by organisms such as cytomegalovirus, *Pneumocystis carinii*, Candida, and other apparently "opportunistic" pathogens, including bacteria, viruses and fungi. Immunosuppression can result from a variety of causes, including viral infections (for example, with the HIV virus), as a result of chemical therapy, and malignancies (particularly of types that affect the hematopoietic system). T-cell immunity is also the major mechanism for rejection of allogeneic tissue or organ transplants. In fact, a major limitation to transplant therapy has been the difficulty in suppressing T-cell allograft rejection reactions without overly compromising vital protective mechanisms.

The adoptive transfer of antigen (Ag)-specific T cells to establish immunity appears to be an effective therapy for some viral infections and tumors in the mouse animal model system. (For a review, See P. D. Greenberg, in *Advances in Immunology* F. Dixon Ed. Academic Press, Inc. Orlando Fla. (1991), pp. 280–355.) However, the efficacy of an adoptive transfer method is dependent upon many factors, including the longevity of the transferred clones and the lack of toxicity to the host of the transferred cells.

Mature T lymphocytes generally express the CD3 cell surface molecule, but consist predominantly of two basic subtypes based on their mutually exclusive expression of cell surface molecules CD4 and CD8. $CD4^+$ T cells are generally involved in "helper" functions in immune responses and secrete cytokine molecules, in particular interleukin 2 (IL-2), upon which the cytotoxic $CD8^+$ T cells are dependent. $CD4^+$ T cells are often referred to as T helper ($T_H$) cells. $CD8^+$ cells are involved in "effector" functions in immune responses, such as direct cytotoxic destruction of target cells bearing foreign antigens, and represent an important mechanism for resistance to viral infections and tumors. The functional distinction between $CD4^+$ and $CD8^+$ T cells is based on the ability of $CD4^+$ cells to recognize antigen presented in association with class II MHC molecules, and $CD8^+$ cells to recognize antigen presented in association with class I MHC molecules. The $CD8^+$ cells that mediate this lytic function are designated cytotoxic T lymphocytes (CTLs). Although most CTL are of the $CD8^+$ phenotype, some CTL of the $CD4^+$ phenotype have been described. Generally, individual CTLs (whether $CD8^+$ or $CD4^+$) are antigen-specific.

Lymphocytes are dependent upon a number of cytokines for proliferation. For example, CTLs are dependent on helper T ($T_H$) cell-derived cytokines, such as IL-2, for growth and proliferation in response to foreign antigens. (Zinkernagel and Doherty, Adv. Immunol. 27:51, 1979; Male et al., Advanced Immunology, Chap. 7, Gower Publ., London, 1987; Jacobson et al., J. Immunol. 133:754, 1984). IL-2, for example, is a potent mitogen for cytotoxic T lymphocytes (Gillis and Smith,. Nature 268:154, 1977), and the combination of antigen and IL-2 causes proliferation of primary $CD8^+$ T cells in vitro. The importance of IL-2 for the growth and maintenance of the $CD8^+$ CTL in vivo has been documented in models of adoptive immunotherapy in which the therapeutic efficacy of transferred anti-retroviral $CD8^+$ cells is enhanced by subsequent administration of IL-2 (Cheever et al., J. Exp. Med. 155:968, 1982; Reddehase et al., J. Virol. 61:3102, 1987). IL4 and IL-7 are also capable of stimulating the proliferation of at least a sub-population of mature $CD8^+$ CTL (Alderson et al., J. Exp. Med. 172:577, 1990).

Due to the specificity of T cells for "non-self" antigens, considerable research has been focused on the use of T cells in treating viral infections and malignant tumors. Cytotoxic T cells specific for a particular type of tumor antigen can be isolated and administered to a patient having the tumor, with the effect that the CTLs ameliorate the tumor. It has been demonstrated, for example, that tumor-specific T cells cannot only be generated to experimental tumors in mice, but also that T cells with apparent tumor specificity can be isolated from cancer patients. Such human tumor infiltrating lymphocytes (TILs) have been expanded in vitro and used to treat cancer patients, generating significant enthusiasm for human adoptive immunotherapy with tumor-specific T cells (Rosenberg et al., N. Engl. J. Med. 319:1767, 1988).

Similar studies using cytotoxic T cells specific for viral antigens have also been conducted in animal models. Human HIV-specific CTL of both the $CD8^+$ (Walker et al., Nature 328:345, 1987; Plata et al., Nature 328:348, 1987) and $CD4^+$ (Siliciano et al., Cell 54:561, 1988) phenotype have been isolated and characterized. HIV-specific $CD8^+$ CTL are classical CTL in that their cytotoxic responses are antigen-specific and MHC-restricted (Walker et al., supra; Chenciner et al., Eur. J. Immuno. 19:1537, 1989; Walker et al., Proc. Natl. Acad. Sci. USA 86:9514, 1989), in common with the numerous mouse and human CTL clones which have been characterized which are specific for viral, tumor or allospecific antigens.

Although many antigen-specific T cell clones have been isolated, the use of tumor-specific T cell clones generated in vitro has been shown to have definite limitations in tumor therapy. It has been demonstrated in several therapeutic models that the efficacy of cytolytic $CD8^+$ T cells is limited by a dependency on exogenous IL-2 (normally produced by $T_H$ cells), a finding that has been substantiated in human adoptive therapy trials in which administration of exogenous IL-2 appears essential for optimal therapeutic efficacy (Rosenberg et al., N. Engl. J. Med. 319:1767;, 1988; Klarnet et al., in Role of Interleukin-2 Activated Killer Cells in Cancer, Lutzova and Herberman (eds.), CRC Press, Florida, Chap. 14, pp. 199–218, 1990). Thus, while in vitro T cell cloning techniques provide a means to generate large numbers of T cells with demonstrable tumor or viral specificity, the full potential of using such antigen-specific T cells in therapy appears to be limited by their dependency on cytokines normally produced by $T_H$ cells.

In some limited instances the problem of $T_H$ dependency may be circumvented by using a particular class of cells known to function independent of $T_H$ cells. These cells are known as helper-independent cytolytic CD8$^+$ cells (HIT$_C$) (Klarnet et al., J. Immunol. 142:2187, 1989) and have been identified in populations of primary (i.e., freshly isolated from in vivo sources) CD8$^+$ CTL (Sprent and Schaefer, J. Exp. Med. 162:21068, 1985; Andrus et al., J. Exp. Med. 159:647, 1984). HIT$_C$ cells produce sufficient IL-2 to grow independently of CD4$^+$ cells and the cytokines they produce. HIT$_C$ cells have been shown to express plasma membrane IL-1 receptors (IL-1R) and require IL-1 for their IL-2-independent proliferation (Klarnet et al., 1989, supra). This is in contrast to conventional CD8$^+$ CTL which do not express detectable IL-1R on their surface (Lowenthal and MacDonald, 1987). HIT$_C$ cells have been generated which are specific for a range of antigens, including tumor, viral and alloantigens (von Boehmer et al., J. Immunol. 133:59, 1984; Klarnet et al., J. Immunol. 138:4012, 1987; and Andrus et al., J. Exp. Med. 149:647, 1984; Mizouchi et al., J. Immunol. 142:270, 1989). HIT$_C$ specific for a retrovirally transformed tumor have been shown to eradicate the tumor cells and persist long-term in vivo following their engraftment (Klarnet et al., 1989, supra). However, analogous human HIT$_C$ cells having specificity for many important antigens, such as HIV, have not yet been isolated.

Realizing the full potential of antigen-specific T cells in therapy would be facilitated by developing a more complete repertoire of lymphocytes, in particular CTLs, with a lessened dependency on $T_H$-cells. One approach has been the introduction of a recombinant vector that expresses a cytokine receptor, for example the IL-1 receptor, into $T_H$-dependent CTL, resulting in the conversion to CTLs with a lessened dependency on IL-2. (PCT/US91/06921, WO 92/05794, published Apr. 16, 1992). The present invention, described below, presents a different approach to the production of lymphocytes with lessened dependency on one or more factors that stimulate growth and proliferation. As a part of the invention, lymphocytes with a lessened dependency on a stimulatory factor are produced via the expression of chimeric cytokine receptors that enable the cells to proliferate despite limiting quantities of a normally required cytokine, for example IL-2. The chimeric receptors contain domains of cytokine receptor chains, for example, IL-2 receptor (IL-2R), fused to domains of heterologous cytokine receptors. Chimeric receptors containing a portion of the IL-2R have been reported. In one chimeric receptor construct, an extracellular domain of IL-2R (now known to correspond to the α-chain) was fused to a transmembrane and intracellular tyrosine kinase domain of epidermal growth factor receptor (EGFR). The polypeptide was expressed in fibroblasts, yielding a product which reportedly had high affinity for IL-2, and which reportedly transformed the fibroblasts. Bernard et al. (1987), Proc. Natl. Acad. Sci. USA 84:2125–2129. However, it has been reported that fibroblastoid cell lines do not respond to IL-2 by proliferation. (Cf. Takeshita et al. (1992), Science 257:379–382, citing S. Minamoto et al. (1990), J. Immunol. 145:2177). In another chimeric construct, the extracellular domain of IL-2R β-chain was fused to the cytoplasmic domain of murine erythropoietin receptor (EPO-R). The resultant construct was reportedly not capable of transducing an IL-2 induced signal. Mori et al. (1991), Int. Immunol. 3:149–156.

SUMMARY OF THE INVENTION

The invention provides polynucleotide constructs encoding chimeric receptors that enable activated lymphocytes, particularly cytotoxic T lymphocytes (CTLs), to proliferate in response to an alternative cytokine other than one that is normally required. Preferably the alternative cytokine is one that is synthesized within the lymphocyte in response to antigen stimulation, which would thereby provide the lymphocyte with regulated autocrine growth. The chimeric constructs expressed from the polynucleotides contain a cytoplasmic region derived from the receptor of the normally required cytokine, for example IL-2R, joined, via a transmembrane domain, to an extracellular domain derived from the alternative cytokine receptor (e.g., GM-CSF-R). These chimera bind the cytokine (e.g., GM-CSF) recognized by the extracellular region of the alternative cytokine receptor (e.g. GM-CSF-R), and transmit the signal that generally occurs when the normal cytokine (e.g., IL-2) binds to its receptor (e.g. IL-2R), resulting in proliferation. The invention also includes the use of the polynucleotides encoding the chimeric receptors to prepare lymphocytes with lessened dependency on a cytokine, and the cells containing the chimeric constructs. The use in immunotherapy of lymphocytes containing polynucleotides encoding the chimeric receptors is also within the scope of the invention.

Accordingly, one embodiment of the invention is a chimeric receptor comprising one or more chimeric peptide chains that have an extracellular domain derived from cytokine receptor A-R that binds cytokine A, joined, via a transmembrane domain, to a cytoplasmic domain derived from cytokine receptor B-R that binds cytokine B, wherein cytokine B is a cytokine that is normally required by a lymphocyte for growth and proliferation and wherein the chimeric receptor expressed in said lymphocyte lessens the growth dependency of the lymphocyte on cytokine B in the presence of cytokine A.

Another embodiment of the invention is a recombinant polynucleotide encoding one or more of the above-described peptide chains. Yet another embodiment is a cell containing such a recombinant polynucleotide. The recombinant polynucleotide may be in the form of a recombinant expression vector. The cell may be a lymphocyte.

Still another embodiment of the invention is a method of using a recombinant polynucleotide comprising a region encoding a first peptide chain, wherein the first peptide chain comprises an extracellular domain derived from cytokine receptor A-R that binds cytokine A, joined, via a transmembrane domain, to a cytoplasmic domain derived from cytokine receptor B-R that binds cytokine B, wherein cytokine B is a cytokine that is normally required by a lymphocyte for growth and proliferation and wherein the chimeric receptor expressed in said lymphocyte lessens the growth dependency of the lymphocyte on cytokine B in the presence of cytokine A, the method comprising transforming a cell with the recombinant polynucleotide.

Yet another embodiment of the invention is a cell produced by the above-described method, and progeny thereof.

DETAILED DESCRIPTION OF THE INVENTION

The invention provides antigen specific lymphocytes that differ from the parental lymphocytes by the presence of a recombinant polynucleotide that encodes a chimeric receptor. The chimeric receptor enables the lymphocytes, to proliferate in response to an alternative cytokine, preferably a cytokine that is expressed in the lymphocyte at elevated levels in response to cognate antigen stimulation, or a cytokine that could be administered with reduced toxicity relative to, e.g., IL-2. The chimeric receptor is a fusion of an extracellular region of one receptor (receptor A-R), via a transmembrane region, to an intracellular region of a second receptor (receptor B-R). As discussed below, the receptor may comprise one or more peptide chains. Binding of cognate cytokine to the extracellular region (derived from receptor A-R) delivers the signal normally associated with receptor B-R. Thus, for example, an activated CTL containing a chimeric GM-CSF:IL-2 receptor, as a result of the CTL production of GM-CSF would proliferate (in response to GM-CSF) in the presence of quantities of IL-2 that would normally be limiting. Cytoplasmic domains of suitable receptors are chosen dependent upon the type of lymphocyte to be stimulated. For example, if the lymphocyte is a CTL, suitable cytoplasmic regions may be obtained from a receptor for a cytokine the lack of which would limit proliferation in the absence of cytokines produced by $T_H$-cells, for example, IL-2. Suitable receptor regions for the extracellular domains can be derived from a receptor recognizing a cytokine that is to be present in non-limiting quantities. For example, for CTLs, the receptors include those that bind granulocyte-macrophage colony stimulating factor (GM-CSF), IL-3, gamma-interferon (IFN-γ) and tumor necrosis factor-beta (TNF-β). As is well known in the art, suitable transmembrane domains will exhibit characteristics such as hydrophobicity that promote their stable incorporation into the cellular membrane. Logically, a convenient source of such a transmembrane domain will be the transmembrane domains of receptors A-R or B-R. Preferably, therefore, the transmembrane domain is derived from cytokine receptor A-R or, more preferably, from receptor B-R. However, a large variety of other transmembrane domains have been described in the art and these can also be used in the invention.

Figure 1:
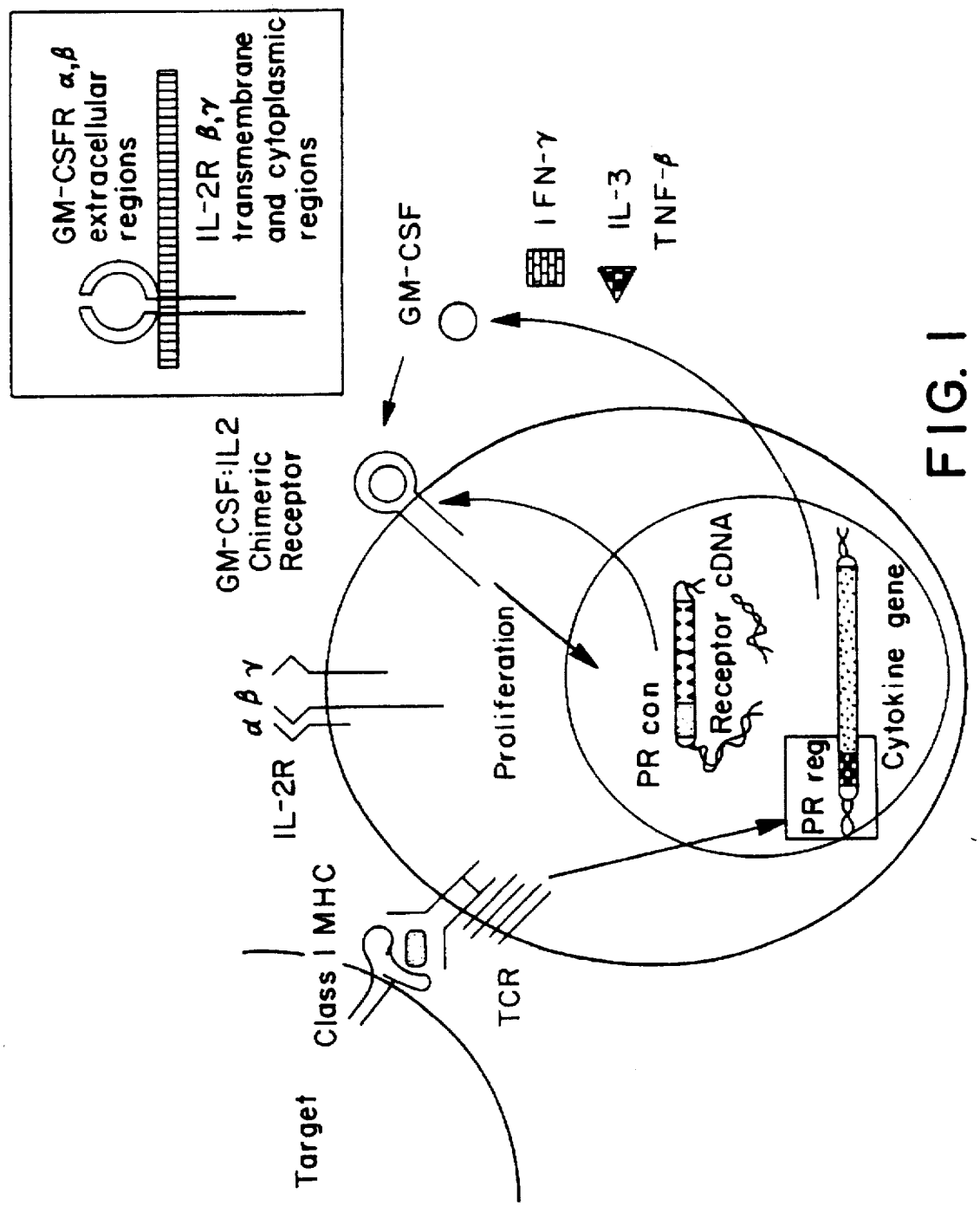
FIG. 1 is an illustration of a prototypic chimeric receptor that can be employed in the overall strategy of the present invention.

A prototypical chimeric receptor is shown in FIG. 1. The receptor consists of the extracellular region of a heterologous cytokine receptor, in the figure the GM-CSF receptor (GM-CSF-R), fused to the transmembrane and cytoplasmic regions of a cytokine receptor recognizing a cytokine that in the absence of $T_H$-cells is normally limiting, in the figure IL-2R. This receptor should bind the heterologous or alternative cytokine (in the figure GM-CSF) extracellularly but deliver the proliferative signal of the cytokine receptor whose cytoplasmic domain is used as part of the chimeric construct. In the construct of FIG. 1, it would be that of the IL-2R. The chimeric receptors may be expressed in the lymphocytes under the control of a constitutive promoter (PRcon), and therefore, always be present on the cell surface. Proliferation of the cells occurs when the cytokine recognized by the extracellular domain binds to the chimeric receptor. If the cytokine is made by the activated lymphocyte, activation creates an autocrine growth loop. In the alternative, it may be desirable to include in the chimeric receptor extracellular domain a receptor fragment that recognizes a cytokine that may be furnished as part of a therapeutic regimen. It may alternatively be desirable to use a promoter that is subject to induction or repression. A variety of such promoters are known in the art.

"Lymphocytes" as used herein, are spherical cells with a large round nucleus (which may be indented) and scanty cytoplasm. They are cells that specifically recognize and respond to non-self antigens, and are responsible for development of specific immunity. Included within "lymphocytes" are B-lymphocytes and T-lymphocytes of various classes.

"Cytotoxic T lymphocytes" or "CTLs" are T cells which bear the CD3 cell surface determinant and mediate the lysis of target cells bearing cognate antigens. CTLs may be of either the $CD8^+$ or $CD4^+$ phenotype. CTLs are generally antigen-specific and MHC-restricted in that they recognize antigenic peptides only in association with the Major Histocompatibility Complex (MHC) molecules on the surface of target cells. CTLs may be specific for a wide range of viral, tumor or allospecific antigens, including HIV, EBV, CMV and a wide range of tumor antigens. Some CTLs, however, may not be antigen specific, for example, some cloned CTLs can be induced to lose some of their specificity for their cognate antigen by culture in abnormally high concentrations of IL-2 (Brooks et al., Immunol. Rev. 72:43, 1983).

A "$T_H$-independent" CTL is, relative to the CTL from which it was derived, capable of enhanced growth or proliferation in the presence of limiting quantities of $CD4^+$ T helper ($T_H$) cells and/or a cytokine normally required for proliferation or growth. Growth or proliferation may be measured, for example, by any in vitro proliferation or growth assay or by any assay measuring the ability of the CTL to persist in vivo. Specific examples of suitable assays are disclosed infra. CTLs capable of enhanced growth or viability may have augmented ability to destroy target cells bearing the foreign antigens or provide long-term immunologic memory.

"Cytokine" refers to a polypeptide that is a soluble intercellular signalling molecule, including for example, the interleukins, interferons, colony stimulating factors and TNFs.

The term "polypeptide" refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as the modifications known in the art, both naturally occurring and non-naturally occurring.

"Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

"Treatment" as used herein refers to prophylaxis and/or therapy.

"Helper T cells" or "helper cells" or "$T_H$-cells" are a functional subclass of T cells which can help to generate cytotoxic T cells and cooperate with B cells in the production of an antibody response. Helper cells usually recognize antigen in association with class II MHC molecules.

An "antigen specific T cell clone" is comprised of the progeny of a single cell; the cells in this type of clone are of the same phenotype and are all targeted towards the same antigen. Methods of preparing antigen-specific T cell clones are known in the art.

The term "recombinant expression vector" refers to a replicable unit of DNA or RNA in a form which is capable of being introduced into a target cell by transformation, electroporation, transduction or viral infection, and which codes for the expression of a heterologous structural coding sequence, for example, a cytokine, which is transcribed into mRNA and translated into protein under the control of elements having a regulatory role in gene expression. Such vectors will preferably also contain appropriate transcription and translation initiation and termination sequences.

"Recombinant," as used herein, means that a particular DNA sequence is the product of various combinations of cloning, restriction, and ligation steps resulting in a construct having a structural coding sequence distinguishable from homologous sequences found in natural systems. Generally, DNA sequences encoding the structural coding sequence, for example cytokines, can be assembled from cDNA fragments and short oligonucleotide linkers, or from a series of oligonucleotides, to provide a synthetic gene which is capable of being expressed in a recombinant transcriptional unit. Such sequences are preferably provided in the form of an open reading frame uninterrupted by internal nontranslated sequences, or introns, which are typically present in eukaryotic genes. Genomic DNA containing the relevant sequences could also be used. Sequences of non-translated DNA may be present 5' or 3' from the open reading frame, where such sequences do not interfere with manipulation or expression of the coding regions.

"Recombinant host cells", "host cells", "cells", "cell lines", "cell cultures", and other such terms denoting microorganisms or higher eukaryotic cell lines cultured as unicellular entities refer to cells which can be, or have been, used as recipients for recombinant vectors or other transfer polynucleotides, and include the progeny of the original cell which has been transfected. It is understood that the progeny of a single cell may not necessarily be completely identical in morphology or in genomic or total DNA complement as the original parent, due to natural, accidental, or deliberate mutation.

A CTL is "cytolytically specific for" cells expressing tumor or viral antigens if the CTL is capable of selectively recognizing and lysing the cells bearing the tumor or viral antigen. A CTL is "cytolytically reactive against" cells expressing tumor or viral antigens if the CTL is capable of lysing the cells bearing the tumor or viral antigen, without regard to its ability to selectively recognize such cells.

"Antigen specific expression" refers to expression that occurs when the T cell recognizes its cognate antigen.

"Cognate antigen" refers to antigen, a peptide of which is associated with an MHC molecule, such that it forms a ligand that binds to a lymphocyte that recognizes it and causes triggering of signals for the effector function of the cell and/or for proliferation.

An "activated lymphocyte" is one that as a result of binding of a cognate antigen is producing polypeptide factors (including, for example, cytokines) at a level that is elevated relative to the lymphocyte without the bound cognate antigen.

A "transcriptional regulatory region" encompasses all the elements necessary for transcription, and may include elements necessary for regulation. Thus, a transcriptional regulatory region includes at least the promoter sequence, and may also include other regulatory sequences such as enhancers, and transcription factor binding sites.

"Operably linked" refers to a juxtaposition wherein the components so described are in a relationship permitting them to function in their intended manner. For instance, a promoter is operably linked to a coding sequence if the promoter affects its transcription or expression.

The term "recombinant" polynucleotide or nucleic acid refers to one which is not naturally occurring, or is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

The "sense strand" of a nucleic acid contains the sequence that has sequence homology to that of the cognate mRNA. The "anti-sense strand" contains a sequence which is complementary to that of the "sense strand".

An "individual" as used herein refers to vertebrates, particularly members of the mammalian species, and includes but is not limited to domestic animals, sports animals, and primates, including humans.

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, Fritsch, and Maniatis, MOLECULAR CLONING: A LABORATORY MANUAL, Second Edition (1989), OLIGONUCLEOTIDE SYNTHESIS (M. J. Gait Ed., 1984), ANIMAL CELL CULTURE (R. I. Freshney, Ed., 1987), the series METHODS IN ENZYMOLOGY (Academic Press, Inc.); GENE TRANSFER VECTORS FOR MAMMALIAN CELLS (J. M. Miller and M. P. Calos eds. 1987), HANDBOOK OF EXPERIMENTAL IMMUNOLOGY, (D. M. Weir and C. C. Blackwell, Eds.), CURRENT PROTOCOLS IN MOLECULAR BIOLOGY (P. M. Ausubel, R. Brent, R. E. Kingston, D. D. Moore, J. G. Siedman, J. A. Smith, and K. Struhl, eds., 1987), and CURRENT PROTOCOLS IN IMMUNOLOGY (J. E. Coligan, A. M. Kruisbeek, D. H. Margulies, E. M. Shevach and W. Strober, eds., 1991). All patents, patent applications, and publications mentioned herein, both supra and infra, are hereby incorporated herein by reference.

The design of some of the chimeric receptors of the invention is as follows, and uses the IL-2R as an illustration. The IL-2R, including human IL-2R, is comprised of three chains, two of which (β and γ) are required for signal transduction. (See Hatakeyama et al. (1989), Science 244:379–382; and Takeshita et al. (1992), Science 257:551–556, for the coding sequences and description of functionality of the IL-2R β and γ chains; see also, Nelson, B. H. et al. (1994) Nature (in press)). Thus, a given chimeric receptor is comprised of two chains containing three regions or domains: cytoplasmic, transmembrane, and extracellular. As will be apparent, the transmembrane domain may conveniently be derived from the same source as the cytoplasmic or the extracellular domain, but transmembrane domains from other sources can likewise be used. In an example based on IL-2, one chain of the chimeric receptor has an IL-2R β chain transmembrane region and cytoplasmic region while the other chain has a γ chain transmembrane region and cytoplasmic region. The number of chain types in the extracellular region of the chimeric receptor depends on the heterologous cytokine receptor selected to contribute to this domain. For example, hetero-oligomeric type cytokine receptors (for example, IL-2R, IL-3R, IL-5R, IFN-γ-R, GM-CSF-R and IL-6-R) require at least two distinct subunit types to form a high affinity receptor. The IL4 and IL-7 receptors are also hetero-oligomeric type receptors in that they have been reported to utilize a second (γ) chain for signalling; which γ chain appears to be the same as that of the IL-2 receptor. (See, e.g., Kondo, M., et al. (1993), Science 262:1874–1877). Other types of cytokine receptors have high affinity ligand binding by itself (i.e. monomeric) or form a high affinity receptor as a homodimer or homo-oligomer (e.g., c-kit-R, TNF-R, Epo-R and G-CSF-R). A discussion of the properties and coding sequences of a number of cytokine receptors is found in a review by Miyajima et al. (1992), Ann. Rev. Immunol. 10:295:331.

Figure 2:
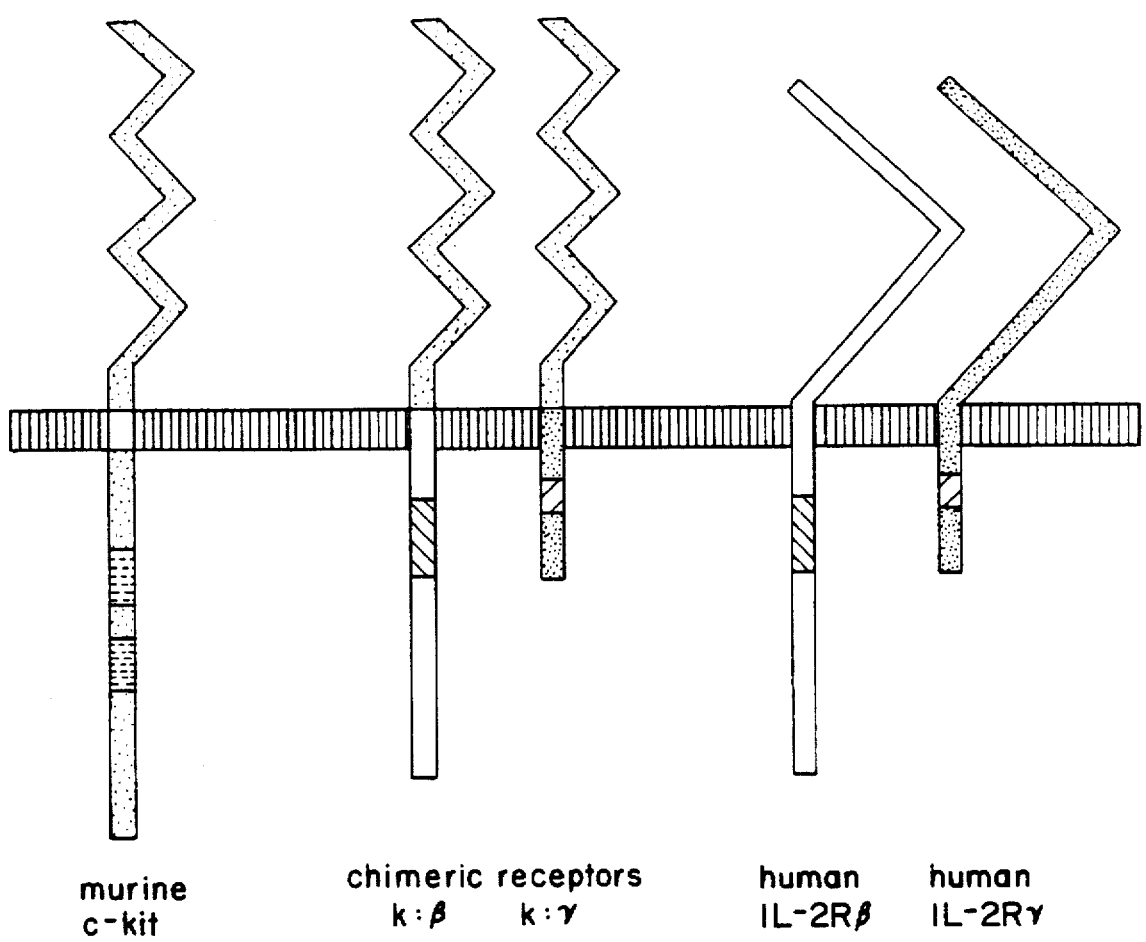
FIG. 2 is an illustration of a prototypic chimeric receptor in which the non-IL-2R extracellular domain is from a cytokine receptor that contains a single type chain, c-kit, attached to two different IL-2-derived intracellular domains.

FIG. 2 illustrates the design of a prototypic chimeric receptor in which the non-IL-2R extracellular domain is from a cytokine receptor that contains a single type chain, for example, c-kit. The figure illustrates the normal c-kit on the left and the normal IL-2R β and γ chains on the right. The middle of the drawing shows a two-chain chimeric receptor containing the extracellular region of c-kit fused to the transmembrane and cytoplasmic region of the IL-2R β chain (k:β) and of the γ chain (k:γ). Other examples of this type of construct can be formed using extracellular domains from other one chain type receptors, e.g., TNF-R and G-CSF-R.

Figure 5:
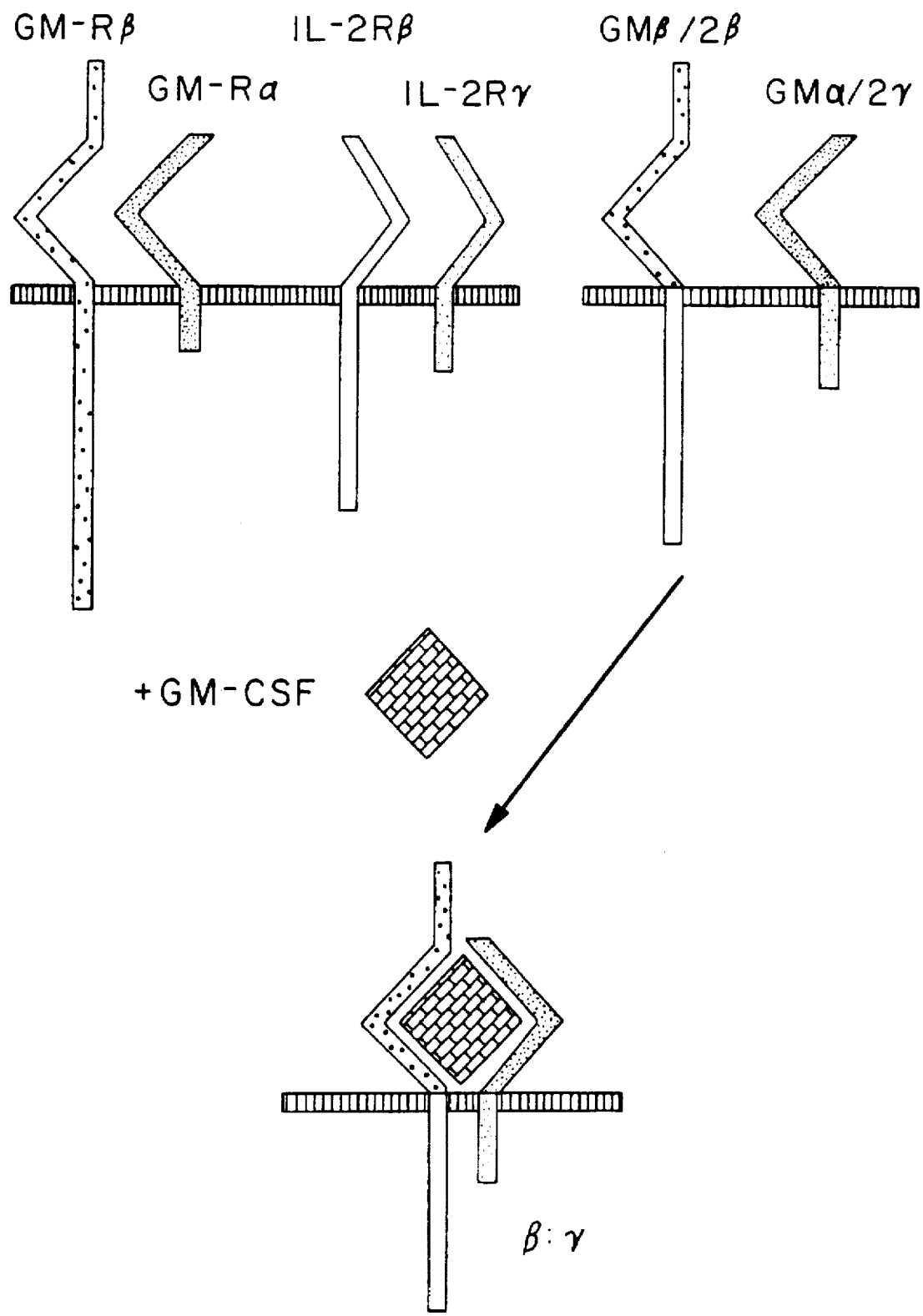
FIG. 5 is a schematic illustration of chimeric GM-CSF/IL-2 receptors. In the upper left, the extracellular region of the human GM-CSF-R α or β chains and the intracellular regions of human IL-2Rβ or IL-2Rγ chains were used to construct chimeric receptors designated GMβ/2β and GMα/2γ, respectively (shown in the upper right); which undergo heterodimerization upon binding GM-CSF (shown in the lower portion of FIG. 5).

An illustration of another type of prototypic chimeric receptor is shown in the inset of FIG. 1. In this illustration the non-IL-2R extracellular domain is from a cytokine receptor that contains two types of chains, for example, GM-CSF-R. In the figure, the extracellular region of the α-subunit of GM-CSF-R is fused to the transmembrane region and cytoplasmic region of the γ chain of IL-2R; the extracellular region of the β-subunit of GM-CSF-R is fused to the transmembrane region and cytoplasmic region of the β chain of IL-2R. See also, the illustration in FIG. 5.

Preferred examples of chimeric receptors contain the cytoplasmic and transmembrane regions of the human IL-2R β and γ chains and extracellular domains derived from the following receptors: human and murine GM-CSF-R; human and murine IFNγ-R; human and murine IL-3R; human and murine G-CSF-R; human and murine IL4R; human and murine IL-7R; human and murine c-kit-R; and human and murine Epo-R.

The chimeric receptors may be constructed from cDNAs encoding the desired segments, although other methods are readily apparent to those of ordinary skill in the art. In one method, for example, the chimeric receptor DNA is prepared by providing cloned cDNAs encoding the upstream extracellular region from a heterologous cytokine receptor and the downstream IL-2R transmembrane and cytoplasmic domains. These cloned cDNAs, if prepared by restriction enzyme digestion, may contain unwanted sequences that would intervene in the fusion. The unwanted sequences are removable by techniques known to those of ordinary skill in the art, including loop-out site-directed mutagenesis or splice-overlap extension polymerase chain reaction (PCR). The sequence of the chimeric cDNA encoding the receptor may then be confirmed by standard DNA sequencing methods. Specific examples of such chimeric receptors are illustrated in more detail below.

The polynucleotide region encoding the chimeric receptors are generally operably linked to control regions that allow expression of the chimeric receptor in a host cell, particularly a CTL. Control regions include, at least, a promoter and a ribosomal binding site, and may also include, inter alia, enhancer regions, splice regions, polyadenylation regions, transcription and/or translation termination regions, and transcription and/or translation factor binding sites. These control regions may be present in recombinant vectors, particularly in recombinant expression vectors.

The ability of the chimeric receptor to support proliferation of the activated CTL is readily demonstrated by techniques known in the art. For example, activated cell lines that express the chimeric receptors can be tested for growth in the absence of the cytokine whose signal is normally associated with the cytoplasmic domain portion of the receptor, but in the presence of the cytokine recognized by the extracellular domain cytokine receptor portion of the chimeric construct.

The invention contemplates transforming lymphocytes with at least one type of chimeric receptor to lessen the dependence upon at least one cytokine. However, it is also within the invention to transform lymphocytes with multiple forms of chimeric receptors that may, for example, regulate the lessened dependency on a cytokine, and/or lessen and/or regulate the dependency on two or more cytokines.

Techniques for nucleic acid manipulation are described generally, for example, in Sambrook et al. (1989), supra., Ausubel et al. (1987), supra. and in Annual Reviews of Biochemistry (1992) 61:131–156. Reagents useful in applying such techniques, such as restriction enzymes and the like, are widely known in the art and commercially available from a number of vendors.

Large amounts of the polynucleotides used to create the cells of the present invention may be produced by replication in a suitable host cell. The natural or synthetic polynucleotide fragments coding for a desired fragment may be incorporated into recombinant nucleic acid constructs, typically polynucleotide constructs, capable of introduction into and replication in a prokaryotic or eukaryotic cell. Usually the constructs will be suitable for replication in a unicellular host, such as yeast or bacteria, but may also be intended for introduction to, with and without and integration within the genome, cultured mammalian or plant or other eukaryotic cell lines. Purification of nucleic acids produced by the methods of the present invention can be achieved by methods known in the art and described, e.g., in Sambrook et al. (1989) and Ausubel et al. (1987).

The polynucleotides used in the present invention may also be produced in part or in total by chemical synthesis, e.g., by the phosphoramidite method described by Beaucage and Carruthers (1981) *Tetra. Letts.* 22:1859–1862 or the triester method according to Matteucci et al. (1981) *J. Am. Chem. Soc.* 103:3185, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

Polynucleotide constructs prepared for introduction into a prokaryotic or eukaryotic host cell for replication will typically comprise a replication system recognized by the host, including the intended recombinant polynucleotide fragment encoding the desired polypeptide. Such vectors may be prepared by means of standard recombinant techniques well known in the art and discussed, for example, in Sambrook et al. (1989) or Ausubel et al.

Preferably, the polynucleotide construct will contain a selectable marker, a gene encoding a protein necessary for the survival or growth of a host cell transformed with the vector. The presence of this gene ensures the growth of only those host cells which express the inserts. Typical selection genes encode proteins that (a) confer resistance to antibiotics or other toxic substances, e.g. ampicillin, neomycin, methotrexate, etc.; (b) complement auxotrophic deficiencies, or (c) supply critical nutrients not available from complex media, e.g. the gene encoding D-alanine racemase for Bacilli. The choice of the proper selectable marker will depend on the host cell, and appropriate markers for different hosts are well known in the art.

The polynucleotides conferring $T_H$-independence upon CTLs (i.e., a lowered dependence upon $T_H$-cells or one or more cytokines furnished by $T_H$ cells) may be introduced into the desired type Ag-specific T cell by means known in the art, including, for example, transformation, electroporation, lipofection, and transduction, including the use of adenoassociated viral (AAV) vectors, and particularly using methods of retroviral gene transfer known in the art.

Various infection techniques have been developed which utilize recombinant infectious virus particles for gene delivery. This represents a preferred approach to the present invention. The viral vectors which have been used in this way include virus vectors derived from simian virus 40 (SV40; Karlsson et al., *Proc. Natl. Acad. Sci. USA* 84 82:158, 1985), adenoviruses (Karlsson et al., *EMBO J.* 5:2377, 1986), adeno-associated virus (AAV) (B. J. Carter, Current Opinion in Biotechnology 1992, 3:533–539), and retroviruses (Coffin, 1985, pp. 17–71 in Weiss et al. (eds.), RNA Tumor Viruses, 2nd ed., Vol. 2, Cold Spring Harbor Laboratory, New York). Thus, gene transfer and expression methods are numerous but essentially function to introduce and express genetic material in mammalian cells. Several of the above techniques have been used to transduce hematopoietic or lymphoid cells, including calcium phosphate transfection (Berman et al., supra, 1984), protoplast fusion (Deans et al., supra, 1984), electroporation (Cann et al., *Oncogene* 3:123, 1988), and infection with recombinant adenovirus (Karlsson et al., supra; Reuther et al., Mol. Cell. Biol. 6:123, 1986), adeno-associated virus (LaFace et al., supra) and retrovirus vectors (Overell et al., *Oncogene* 4:1425, 1989). Primary T lymphocytes have been successfully transduced by electroporation (Cann et al., supra, 1988) and by retroviral infection (Nishihara et al., *Cancer Res.* 48:4730, 1988; Kasid et al., supra, 1990; and Riddell, S. et al., Human Gene Therapy 3:319–338, 1992).

Retroviral vectors provide a highly efficient method for gene transfer into eukaryotic cells and is the preferred method for the delivery of the polynucleotides of the invention into the $T_H$-dependent CTLs. Moreover, retroviral integration takes place in a controlled fashion and results in the stable integration of one or a few copies of the new genetic information per cell.

Retroviruses are a class of viruses which replicate using a virus-encoded, RNA-directed DNA polymerase, or reverse transcriptase, to replicate a viral RNA genome to provide a double-stranded DNA intermediate which is incorporated into chromosomal DNA of an avian or mammalian host cell. Most retroviral vectors are derived from murine retroviruses. Retroviruses adaptable for use in accordance with the present invention can, however, be derived from any avian or mammalian cell source. These retroviruses are preferably amphotropic, meaning that they are capable of infecting host cells of several species, including humans. A characteristic feature of retroviral genomes (and retroviral vectors used as described herein) is the retroviral long terminal repeat, or LTR, which is an untranslated region of about 600 base pairs found in slightly variant forms at the 5' and 3' ends of the retroviral genome. When incorporated into DNA as a provirus, the retroviral LTR includes a short direct repeat sequence at each end and signals for initiation of transcription by RNA polymerase II and 3' cleavage and polyadenylation of RNA transcripts. The LTR contains all other cis-acting sequences necessary for viral replication.

A "provirus" refers to the DNA reverse transcript of a retrovirus which is stably integrated into chromosomal DNA in a suitable host cell, or a cloned copy thereof, or a cloned copy of unintegrated intermediate forms of retroviral DNA. Forward transcription of the provirus and assembly into infectious virus occurs in the presence of an appropriate helper virus or in a cell line containing appropriate sequences enabling encapsidation without coincident production of a contaminating helper virus. Mann et al. (Cell 33:153, 1983) describe the development of cell lines (e.g., Ψ2) which can be used to produce helper-free stocks of recombinant retrovirus. These cells lines contain integrated retroviral genomes which lack sequences required in cis for encapsidation, but which provide all necessary gene product in trans to produce intact virions. The RNA transcribed from the integrated mutant provirus cannot itself be packaged, but these cells can encapsidate RNA transcribed from a recombinant retrovirus introduced into the same cell. The resulting virus particles are infectious, but replication-defective, rendering them useful vectors which are unable to produce infectious virus following introduction into a cell lacking the complementary genetic information enabling encapsidation. Encapsidation in a cell line harboring trans-acting elements encoding an ecotropic viral envelope (e.g., Ψ2) provides ecotropic (limited host range) progeny virus. Alternatively, assembly in a cell line containing amphotropic packaging genes (e.g., PA317, ATCC CRL 9078; Miller and Buttimore, Mol. Cell. Biol. 6:2895, 1986) provides amphitropic (broad host range) progeny virus. Such packing cell lines provide the necessary retroviral gag, pol and env proteins in trans. This strategy results in the production of retroviral particles which are highly infectious for mammalian cells, while being incapable of further replication after they have integrated into the genome of the target cell. The product of the env gene is responsible for the binding of the retrovirus to viral receptors on the surface of the target cell and therefore determines the host range of the retrovirus. The PA 317 cells produce retroviral particles with an amphotropic envelope protein, which can transduce cells of human and other species origin. Other packaging cell lines produce particles with ecotropic envelope proteins, which are able to transduce only mouse and rat cells.

Numerous retroviral vector constructs have been used successfully to express many foreign genes (see, e.g., Coffin, in Weiss et al. (eds.), RNA Tumor Viruses, 2nd ed., vol. 2 (Cold Spring Harbor Laboratory, New York, 1985, pp. 17–71). Retroviral vectors with inserted sequences are generally functional, and few sequences that are consistently inhibitory for retroviral infection have been identified. Functional polyadenylation motifs inhibit retroviral replication by blocking retroviral RNA synthesis, and there is an upper size limit of approximately 11 kb of sequence which can be packaged into retroviral particles (Coffin, supra, 1985); however, the presence of multiple internal promoters, initially thought to be problematic (Coffin, supra, 1985), was found to be well tolerated in several retroviral constructs (Overell et al., Mol. Cell. Biol. 8:1803, 1983).

Retroviral vectors have been used as genetic tags by several groups to follow the development of murine hematopoietic stem cells which have been transduced in vitro with retrovirus vectors and transplanted into recipient mice (Williams et al., Nature 310:476, 1984; Dick et al., Cell 42:71, 1985; Keller et al., Nature 318:149, 1985). These studies have demonstrated that the infected hematopoietic cells reconstitute the hematopoietic and lymphoid tissue of the recipient animals and that the cells display a normal developmental potential in vivo. The marked cells can be visualized using any of a number of molecular biological techniques which can demonstrate the presence of the retroviral vector sequences, most notably Southern analysis and PCR (polymerase chain reaction). The ability to mark cells genetically using retroviral vectors is also useful in clinical settings in which the technique can be used to track grafts of autologous cells. This approach has already been used to track TILs (tumor-infiltrating lymphocytes) in patients given TIL therapy for terminal cancer treatment by Rosenberg et al. (N. Engl. J. Med. 323:570, 1990). The transduction of these cells with the marker gene was not associated with in vitro cellular dysfunction (Kasid et al., Proc. Natl. Acad. Sci. USA 87:473, 1990).

Many gene products have been expressed in retroviral vectors. This can either be achieved by placing the sequences to be expressed under the transcriptional control of the promoter incorporated in the retroviral LTR, or by placing them under the control of a heterologous promoter inserted between the LTRs. The latter strategy provides a way of coexpressing a dominant selectable marker gene in the vector, thus allowing selection of cells which are expressing specific vector sequences.

It is contemplated that overexpression of a stimulatory factor (for example, a lymphokine or a cytokine) may be toxic to the treated individual. Therefore, it is within the scope of the invention to include gene segments that cause the T cell clones of the invention to be susceptible to negative selection in vivo. By "negative selection" is meant that the infused cell can be eliminated as a result of a change in the in vivo condition of the individual. The negative selectable phenotype may result from the insertion of a gene that confers sensitivity to an administered agent, for example, a compound. Negative selectable genes are known in the art, and include, inter alia the following: the Herpes simplex virus type I thymidine kinase (HSV-I TK) gene (Wigler et al., Cell 11:223, 1977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In addition, it is useful to include in the T cells a positive marker that enables the selection of cells of the negative selectable phenotype in vitro. The positive selectable marker may be a gene which, upon being introduced into the host cell expresses a dominant phenotype permitting positive selection of cells carrying the gene. Genes of this type are known in the art, and include, inter alia, hygromycin-B phosphotransferase gene (hph) which confers resistance to hygromycin B, the aminoglycoside phosphotransferase gene (neo or aph) from Tn5 which codes for resistance to the antibiotic G418, the dihydrofolate reductase (DHFR) gene, the adenosine daminase gene (ADA), and the multi-drug resistance (MDR) gene.

Preferably, the positive selectable marker and the negative selectable element are linked such that loss of the negative selectable element necessarily also is accompanied by loss of the positive selectable marker. Even more preferably, the positive and negative selectable markers are fused so that loss of one obligatorily leads to loss of the other. An example of a fused polynucleotide that yields as an expression product a polypeptide that confers both the desired positive and negative selection features described above is a hygromycin phosphotransferase thymidine kinase fusion gene (HyTK). Expression of this gene yields a polypeptide that confers hygromycin B resistance for positive selection in vitro, and ganciclovir sensitivity for negative selection in vivo. See Lupton S. D., et al, Mol. and Cell. Biology 11:3374–3378, 1991. In addition, in preferred embodiments, the polynucleotides of the invention encoding the chimeric receptors are in retroviral vectors containing the fused gene, particularly those that confer hygromycin B resistance for positive selection in vitro, and ganciclovir sensitivity for negative selection in vivo, for example the HyTK retroviral vector described in Lupton, S. D. et al. (1991), supra. See, also, the description of Bifunctional Selectable Fusion Genes by Lupton, S.D., WO 92/08796 (international publication date 29 May 1992).

The lymphocyte clones of the invention may be used to confer immunity to individuals. By "immunity" is meant a lessening of one or more physical symptoms associated with a response to infection by a pathogen, or to a tumor, to which the lymphocyte response is directed. The amount of cells administered is usually in the range present in normal individuals with immunity to the pathogen. Thus, CD8+ CD4− cells are usually administered by infusion, with each infusion in a range of at least $10^6$ to $10^{10}$ cells/m², preferably in the range of at least $10^7$ to $10^9$ cells/m². The clones may be administered by a single infusion, or by multiple infusions over a range of time. However, since different individuals are expected to vary in responsiveness, the type and amount of cells infused, as well as the number of infusions and the time range over which multiple infusions are given are determined by the attending physician or veterinarian, and can be determined by routine examination.

The examples presented below are provided as a further guide to the practitioner of ordinary skill in the art, and are not to be construed as limiting the invention in any way.

EXAMPLE 1

Construction of c-kit:IL-2Rβ

An XhoI-BamH1 fragment of human IL-2Rβ cDNA encompassing most of the extracellular coding region and the entire transmembrane and cytoplasmic regions was cloned into the Xho1 and BamH1 sites of a modified version of the plasmid pBluescript SK- (Stratagene) in which the Not1-Sac1 region had been cleaved out, blunt-ended and religated. (Human IL-2Rβ cDNA (see, e.g., Hatakeyama, M., et al. (1989), Science 244:551–556) was provided by Tada Taniguchi, Osaka, Japan.) This plasmid was then digested with Kpn1 and HincII, and the 199 bp fragment was replaced with a 1995 bp Kpn1-blunted Apa1 fragment of murine c-kit cDNA encompassing the entire extracellular and transmembrane coding regions and a portion of the cytoplasmic coding region. (Murine c-kit cDNA (see, e.g., Qiu, F. et al. (1988) EMBO J. 7:1003–1011) was provided by Stewart Lyman, Immunex Corp., Seattle, Wash.) The resultant plasmid, pBKβ, thus had most of the c-kit cDNA upstream of most of the IL-2Rβ cDNA. The fusion was completed by site-directed looping-out mutagenesis. A uracil-containing single-stranded form of this plasmid was prepared using a Muta-Gene Phagemid In Vitro Mutagenesis kit (BioRad) according to the manufacturer's instructions. This was annealed to a fusion primer with the sequence: 5' GCC GAG CCA CGG AAT GTG GGC CTG GAT TTG 3' (SEQ ID NO:1). Second strand synthesis, ligation, and transformation of E. coli with the annealed product was carried out according to the manufacturer's instructions. The resulting plasmid in which the unwanted intervening cDNA sequences had been successfully removed was digested with HincII and SacI and the 859 bp fragment encompassing the fusion site was cloned back into the parent plasmid, pBKβ which had been similarly digested. This last step minimized the amount of cDNA sequence that had been through the mutagenesis steps, which are error-prone. The sequence of the final plasmid, pBkβ-EX, was confirmed by standard DNA sequencing methods.

A 2524 bp Kpn1 (blunted)-BamH1 (partial digest) fragment from pBkβ-EX that encompassed the entire coding region of the k:β chimeric cDNA was cloned into the expression vector pHβAPr-1-neo (Gunning, P. et al. (1987), P.N.A.S. 84:4831–4835) which had been digested with Sal1 (blunted) and BamH1. This plasmid, called pNkβ, was then transfected into cells.

EXAMPLE 2

Construction of c-kit:IL-2Rγ

A fragment of human IL-2Rγ cDNA (Takeshita, T. et al. (1992), Science 257:379–382) was PCR amplified from second strand cDNA derived from the human T cell clone 2D5 using the primers 5' CCGTTGAC CCC ACT CTG TGG AAG TGC 3' (SEQ ID NO:2) and 5' CCGGATCC GGC TAC AGG ACC CTG GGG 3' (SEQ ID NO:3) (the underlined bases encode restriction enzyme sites). The product was then cloned into the HincII and BamH1 sites of the modified pBluescript SK-plasmid described above and was subjected to DNA sequencing. This plasmid was then digested with Kpn1 and HincII, and the 199 bp fragment was replaced with a 1995 bp Kpn1-blunted Apa1 fragment of murine c-kit cDNA encompassing the entire extracellular and transmembrane coding regions and a portion of the cytoplasmic coding region. The resultant plasmid, pBky, thus had most of the c-kit cDNA upstream of most of the IL-2Rγ cDNA. The fusion was completed by PCR splice-overlap extension. The portion of the plasmid encoding the c-kit extracellular region was amplified by PCR using primers A (CCG AGC ACC AGC AGT GG) (SEQ ID NO:4) and B (TGC AAA CAG GAA AGG GTG GGC CTG GAT TTG) (SEQ ID NO:5). The underlined region of primer B is actually complementary to the transmembrane region of IL-2Rγ. The IL-2Rγ transmembrane and cytoplasmic coding regions were amplified from pBky by PCR using primers C (CAA ATC CAG GCC CAC CCT TTC CTG TTT GCA) (SEQ ID NO:6) and D (CCGGATCC GGG GTT CAG GTT TCA GGC) (SEQ ID NO:7). Note that primer C is entirely complementary to primer B, and together they encode the desired fusion site. The products of these two PCR reactions were then combined in a single tube where they served as substrates in a third PCR reaction using primers A and D. The complementarity of primers B and C allows the products of the first two PCR reactions to anneal to each other and generate an overlap-extended template. The product of the third PCR reaction thus encoded a chimeric cDNA with the desired fusion site and extending from the annealing site of primer A to that of primer D. This product was then digested with BstX1 and Pst1 to generate an 879 bp fragment that was cloned back into pBky, which had been similarly digested. The sequence of the final plasmid, pBky-EX, was confirmed by standard DNA sequencing methods.

A 1977 bp Kpn1 (blunted)-BamH1 (partial digest) fragment from pBky-EX that encompassed the entire coding region of the k:γ chimeric cDNA was cloned into the expression vector pHβAPr-1-hygro which had been digested with Sal1 (blunted) and BamH1 (the expression vector pHβAPr-1-hygro contains the hygromycin sequence derived from RSV.5 (Long, E. O. et al. (1991) Human Immunology 31:229–235) cloned into the expression vector pHβAPr-1-neo, described above). The resulting plasmid, called pHky, was then transfected into cells.

EXAMPLE 3

Construction of pNkit

The cDNA encoding wild type murine c-kit was cloned into the expression vector pHβaPr-1-neo by ligating a blunt-ended 2970 bp Kpn1-Not1 fragment containing the entire c-kit coding region into pHβAPr-1-neo which had been digested with HindIII, blunt-ended and dephosphorylated.

EXAMPLE 4

Modification of Cytokine Dependence in a Cytotoxic T Lymphocyte Cell Line

Expression in T cells

T cells are transfected with plasmids encoding the chimeric receptor, and drug-resistant cell lines selected. To test for expression of the chimeric receptors, drug-resistant cell lines are stained with antibody that recognizes the extracellular region and are scanned by flow cytometry. Expression can also be detected by Western blotting.

Cell lines that express the chimeric receptors are tested for growth in response to the cognate alternative cytokine (i.e., the one recognized by the extracellular domain of the chimeric receptor) in the presence of limiting amounts of the cytokine normally required for growth and/or proliferation, e.g., IL-2.

T cell transfections

Plasmids were linearized by digestion with EcoR1 (for pNkβ and pNkit) or Xmn1 (for pHky) and then purified by phenol-chloroform extraction followed by ethanol precipitation. They were resuspended in distilled water to a concentration of 1 microgram per microliter.

10 million CTLL2 cells were washed once with PBS and then resuspended in 0.8 ml PBS. Twenty-five micrograms of linearized plasmid was added, and the cells left at room temperature for 10 minutes. Doubly transfected cells (i.e. pNkβ and pHkγ) received 25 micrograms of each plasmid. The cells were then placed in a cuvette and electroporated at 250V.1080 µF for one second at room temperature. The cells were then placed in complete media (Click's+10% FCS, 1% glutamine, 1% pen-strep) at 37° C. for 16–20 hours. At this time, the cells were spun down, resuspended in fresh media and incubated at 37° C. for 24 additional hours. Forty-eight hours post-transfection, cells were selected by the addition of neomycin (1 mg/ml) for groups pNkit, pNkβ+pHkγ or hygromycin B (0.5 mg/ml) for the pHkγ group. Drug-resistant cell lines typically grew out in one to two weeks. In the case of the pNkβ+pHkγ cells, the neomycin resistant line was then further selected by removing IL-2 and adding recombinant murine stem cell factor (200 ng/ml) to the cultures.

Flow cytometry 500,000 to one million cells were washed twice in staining solution (Hank's media containing 2% fetal calf serum) and resuspended in 0.1 ml staining solution. One microgram of the monoclonal antibody ACK-2 (Gibco/BRL) which recognizes the extracellular region of murine c-kit was added and the cells were left on ice for 30 minutes. After one wash with staining solution, the cells were resuspended in 0.1 ml staining solution containing a fluorescein-conjugated goat anti-rat secondary antibody (Tago Immunochemicals) and left on ice for thirty minutes. After one wash in staining solution the cells were resuspended in 0.25 ml 0.5% paraformaldehyde.

The fluorescent intensity of the cells was measured using a Becton-Dickinson FACS Scanner.

Proliferation assay

CTLL2 lines were washed twice in RPM1 and resuspended in complete medium (Click's+10% FCS, 1% glutamine, 1% pen-step) at a concentration of 20,000 per ml. Cells were plated in flat-bottom 96-well plates, 0.2 ml per well, with either no added cytokines, or recombinant human IL-2 (100 units./ml), or recombinant murine stem cell factor (200 ng/ml) and incubated at 37° C. for 20 hours. Then 2.5 microcuries of tritiated thymidine was added and the incubation continued for an additional 4 hours. Cells were harvested, placed in scintillation fluid, and incorporated thymidine was measured using a scintillation counter.

Results

Figure 3:
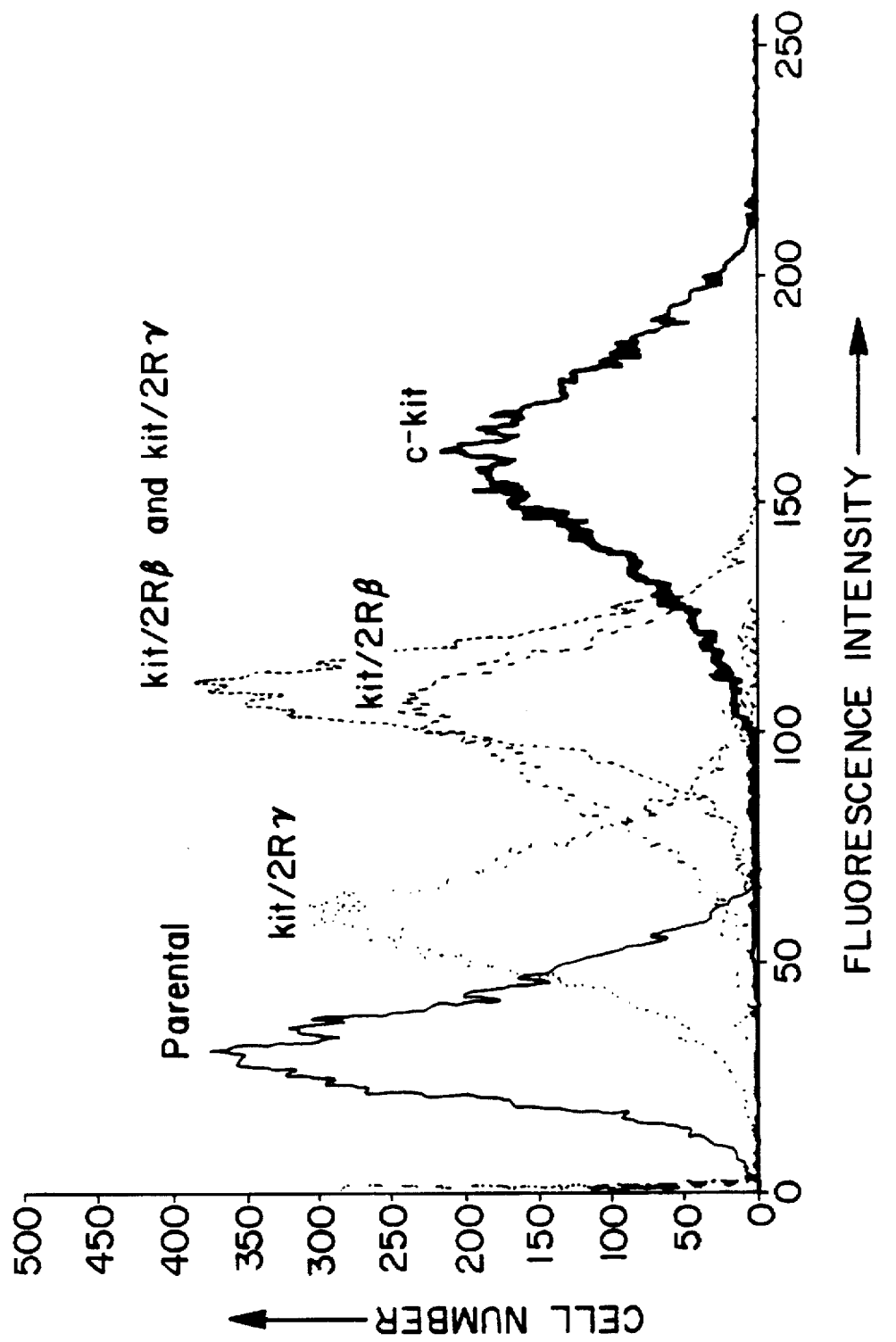
FIG. 3 is a graph showing a trace of fluorescent scanning for surface expression of transfected receptors on CTLL2 cells.

The results provide evidence that the c-kit:IL-2 chimeric receptor is functional. FIG. 3 shows a flow cytometric analysis of the expression of the chimeric receptors in CTLL2, a mouse T cell line that is highly IL-2 dependent for growth and survival. The cells were stained with an antibody against c-kit. The parental cell line is negative for c-kit, whereas cells transfected with k:γ alone, k:β alone, and k:γ and k:β together, or normal c-kit alone are all positive.

Figure 4:
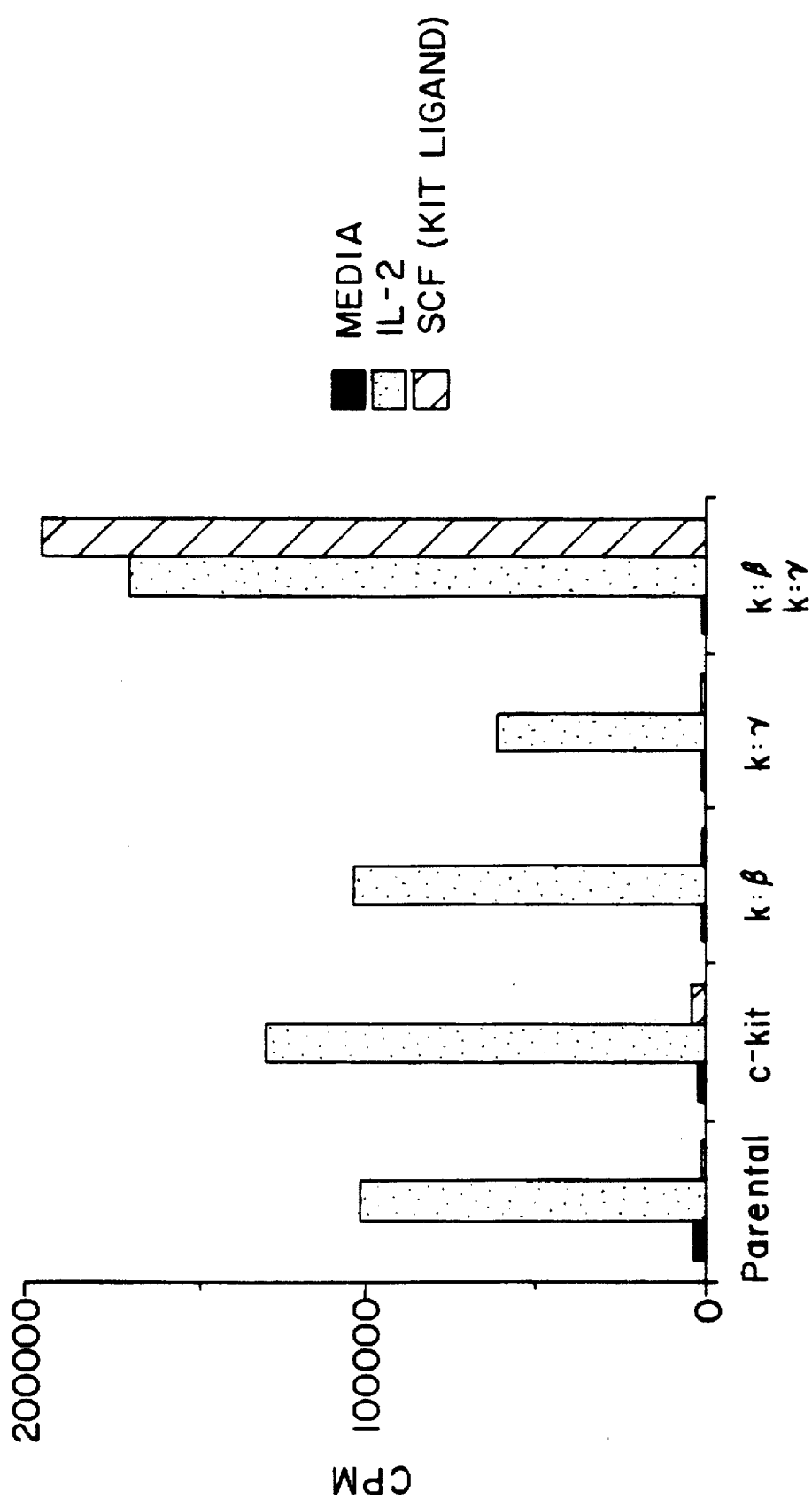
FIG. 4 is a graph showing the effect of ligands on the proliferation of CTLL2 cells transfected with c-kit/IL-2R chimeras.

FIG. 4 shows the proliferative response of these cells to murine stem cell factor (SCF), the natural ligand for c-kit. All the cell lines respond to IL-2. Significantly, cells expressing both k:β and k:γ also respond to SCF. Normal CTLL2 cells die within 24 hours of withdrawal from IL-2. However, the k:β/k:γ transfectants have been maintained for more than a year in the presence of SCF and absence of exogenously added IL-2.

EXAMPLE 5

Modification of Cytokine Dependence in a pro-B Cell Line

Similar results to those described in Example 4, were obtained when k:β/k:γ chimeric receptors were expressed in BAF3 cells (a murine pro-B cell in which growth is normally responsive to IL-3, but responsive to IL-2 if IL-2R is expressed from a transfected in gene).

Some cell proliferation was also observed in BAF3 cells transfected with k:β chains alone. However, a significant indicator of the generation of a normal IL-2 response is the up-regulation of IL-2Rα (See, e.g., Smith, K. A. et al. (1985) P.N.A.S. 82:864–868). Both CTLL2 and BAF3 cells exhibited up-regulation of IL-2Rα when transfected with a combination of k:β and k:γ chains. Neither CTLL2 nor BAF3 cells exhibited up-regulation of IL-2Rα when transfected with k:β chains alone, nor with k:γ chains alone. These results tend to confirm that, for recreating the normal intracellular response of receptors having hetero-oligomeric signalling chains, like the β and γ chains of the IL-2 receptor, it is preferable to incorporate each type of cytoplasmic domain into the chimeric receptors, as described above.

EXAMPLE 6

Modification of Cytokine Dependence in a Helper T Lymphocyte Line

Similar results to those described in Example 4, were obtained when the chimeric receptors were expressed in D10.G4.1 cells. The latter cells are from a murine CD4$^+$ helper T cell clone which normally requires IL-2 for growth. See Kaye et al. (1983), J. Exp. Med. 158:836–856.

EXAMPLE 7

Modification of Cytokine Dependence in a Murine CD8+ CTL Line

Similar results to those described in Example 4, were obtained when the chimeric receptors were expressed in L3 cells. The latter cells are from a murine CD8$^+$ T cell clone. See Siu, G. et al. (1992), Molec. Cell Biol. 12:1592–1604.

The principles and teachings described above have been applied to produce additional embodiments, some of which are described below, further demonstrating the utility of this invention. Included, for example, are additional chimeric receptors demonstrating the usefulness of the invention in T lymphocytes.

EXAMPLE 8

Construction of GMβ/2β

An Xho1-BamH1 fragment of human IL-2Rβ cDNA encoding most of the extracellular coding region and the entire transmembrane and cytoplasmic regions was cloned into the Xho1 and BamH1 sites of a modified version of the plasmid pBluescript SK-(Strategene) in which the Not1-Sac1 region had been cleaved out, blunt-ended and religated. This plasmid was then digested with Kpn1 and HincII, and ligated to an Xho1/blunted EcoR1 fragment of cDNA encoding the entire extracellular and transmembrane coding regions of human GM-CSF-Rβ (KH97) (Hayashida, K. et al. (1990) P.N.A.S. 87:9655–9659). Exact fusions between extracellular and transmembrane regions were made by overlap extension PCR using the complementary fusion primers GCCGAGCCACGGAATCGACTCGGTGTCCCA (SEQ ID NO:8) and TGGGACACCGAGTCGATTCCGTG-GCTCGGC (SEQ ID NO:9). The entire coding region of the GMβ/2β chimeric cDNA was cloned into the expression vector pHβAPr-1-neo, generating the plasmid pNGβ. Fusion sites and flanking regions of the GMβ/2β construct were confirmed by standard DNA sequencing methods.

EXAMPLE 9

Construction of GMα/2γ

A fragment of human IL-2Rγ cDNA was PCR amplified from second strand cDNA derived from the human T cell clone 2D5 using the primers 5' CCGTTGAC CCC ACT CTG TGG AAG TGC 3' (SEQ ID NO:2) and 5' CCGGATCC GGC TAC AGG ACC CTG GGG 3' (SEQ ID NO:3) (the underlined bases encode restriction enzyme sites.) The product was then cloned into the HincII and BamH1 sites of the modified pBluescript SK- plasmid described above and was subjected to DNA sequencing. This plasmid was then digested with Xho1 and HincII, and ligated to an Xho1/blunted EcoR1 fragment of human GM-CSF-Rα cDNA (Gearing, D. P. et al. (1989) EMBO J. 8:3667–3676) encoding the entire extracellular and transmembrane coding regions and a portion of the cytoplasmic coding region. Exact fusions between extracellular and transmembrane regions were made by overlap extension PCR using the complementary fusion primers. TGCAAACAGGAAAGGCCCGTCGTCAGAACC (SEQ ID NO:10) and GGTTCTGACGACGGGCCTTTCCTGTTTGCA (SEQ ID NO:11). The entire coding region of the GMα/2γ chimeric cDNA was cloned into the expression vector pHβAPr-1-hygro, generating the plasmid pHGγ. Fusion sites and flanking regions of the GMα/2γ construct were confirmed by standard DNA sequencing methods.

EXAMPLE 10

Modification of Cytokine Dependence in a Cytotoxic T Lymphocyte Cell Line

T Cell Transfections

Plasmids were linearized by digestion with EcoR1 (for pNGβ) or Xmn1 (for pHGγ) and purified by phenol-chloroform extraction followed by ethanol precipitation. They were resuspended in distilled water to a concentration of 1 microgram per microliter.

10 million CTLL2 cells were washed once with PBS and then resuspended in 0.8 ml PBS. Twenty-five micrograms of linearized plasmid was added, and the cells left at room temperature for 10 minutes. The cells were then placed in a cuvette and electroporated at 250V, 980 µF for one second at room temperature. The cells were then placed in complete media (Click's+10% FCS, 1% glutamine, 1% pen-strep) at 37° C. for 16–20 hours. At this time, the cells were spun down, resuspended in fresh media and incubated at 37° C. for 24 additional hours. Forty-eight hours post-transfection, cells were selected by the addition of neomycin (1 mg/ml) for pNGβ or hygromycin B (0.5 mg/ml) for pHGγ. Drug-resistant cell lines typically grew out in one to two weeks. To generate cells expressing both GMβ/2β and GMα/2γ, the neomycin resistant line expressing GMβ/2β was electroporated with the plasmid pHGγ and then selected for expression of GMα/2γ by removing IL-2 and adding recombinant human GM-CSF (100 ng/ml) to the cultures.

Proliferation Assays

CTLL2 lines were washed twice in RPMI and resuspended in complete medium (Click's+10% FCS, 1% glutamine, 1% pen-strep) at a concentration of 20,000 per ml. Cells were plated in flat-bottom 96-well plates, 0.2 ml per well, with either no added cytokines, or recombinant human IL-2 (5 units/ml), or recombinant human GM-CSF (10 ng/ml) and incubated at 37° C. for 20 hours. Then 2.5 microcuries of tritiated thymidine was added and the incubation continued for an additional 4 hours. Cells were harvested, placed in scintillation fluid, and incorporated thymidine was measured using a scintillation counter.

Figure 6:
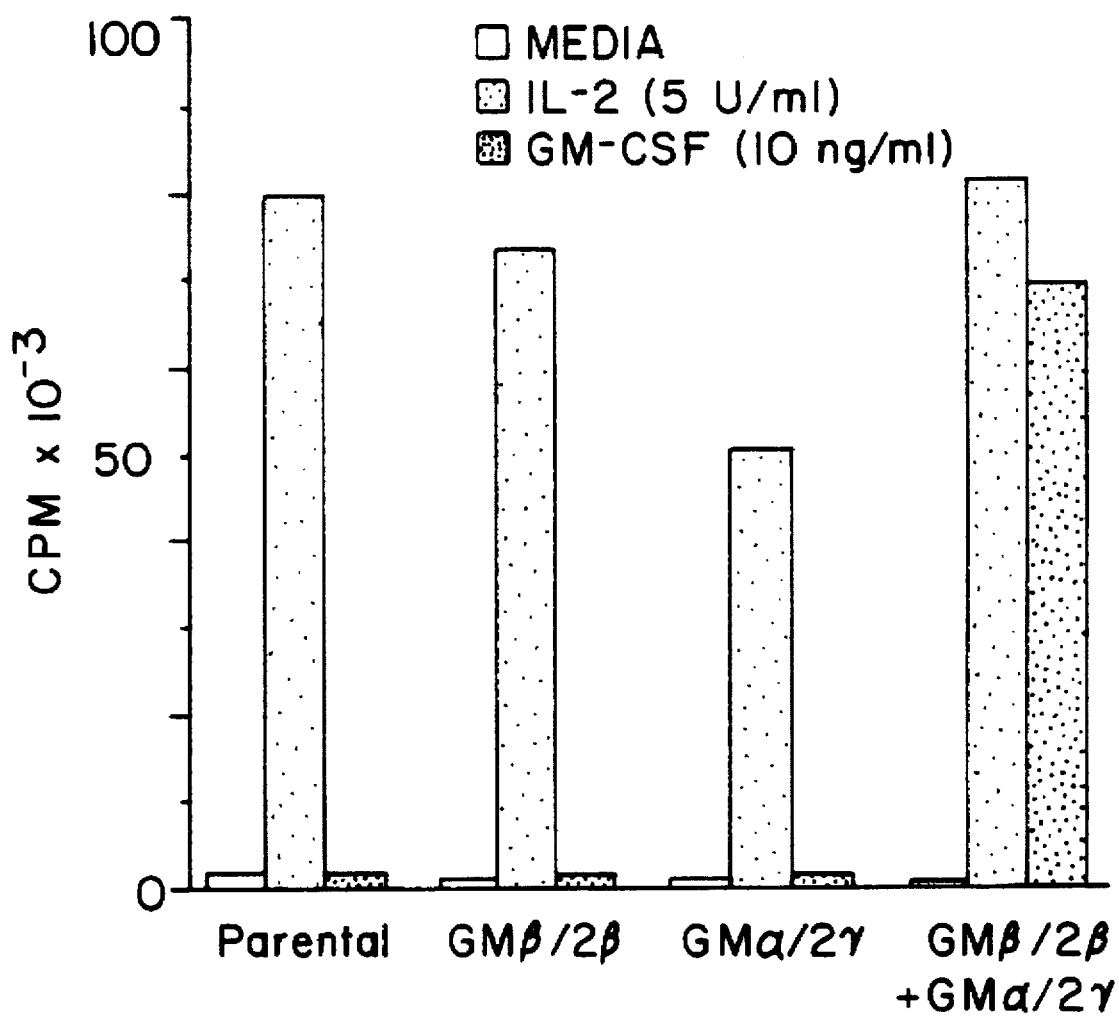
FIG. 6 is a graph showing IL-2- and GM-CSF-induced proliferative responses of the parental (CTLL2) T cell line and of transfectants expressing GMβ/2β or GMα/2γ, or co-expressing GMβ/2β, and GMα/2γ.

FIG. 6 shows the proliferative response of these cells to IL-2 and GM-CSF. All of the cell lines respond to IL-2. Significantly, cells expressing both GMβ/2β and GMα/2γ exhibit a proliferative response to GM-CSF, further demonstrating the usefulness of the invention.

Utility

The polynucleotides of the invention that encode chimeric receptors are useful for the production of lymphocytes that have a lessened requirement for one or more cytokines for proliferation. The cells containing the chimeric receptors with a lessened dependence on one or more cytokines are useful in, inter alia, immunotherapy.

---

We claim:

1. A chimeric receptor comprising a first chimeric peptide chain, said first peptide chain comprising an extracellular domain derived from cytokine receptor A-R that binds cytokine A, joined, via a transmembrane domain, to a cytoplasmic domain derived from cytokine receptor B-R that binds cytokine B, where cytokine receptor A-R and cytokine receptor B-R are different receptors, wherein cytokine B is a cytokine that is normally required by a lymphocyte for growth and proliferation and wherein the chimeric receptor expressed in said lymphocyte lessens the growth dependency of the lymphocyte on cytokine B in the presence of cytokine A and wherein, if cytokine receptor A-R or B-R is hetero-oligomeric, then the chimeric receptor comprises at least first and second of said peptide chains, wherein said peptide chains are different from each other and are each chimeric.

2. The chimeric receptor of claim 1, wherein said cytokine receptor B-R normally comprises two peptide chains that are required for signal transduction, and wherein said chimeric receptor comprises a second peptide chain, said second peptide chain comprising a cytoplasmic domain derived from cytokine receptor B-R.

3. The chimeric receptor of claim 2, wherein said second peptide chain comprises an extracellular domain derived from cytokine receptor A-R that binds cytokine A, joined, via a transmembrane domain, to a cytoplasmic domain derived from cytokine receptor B-R that binds cytokine B.

4. The chimeric receptor of claim 3, wherein cytokine receptor B-R is a hetero-oligomeric type cytokine receptor and wherein the cytoplasmic domain of said second peptide chain is different from the cytoplasmic domain of said first peptide chain.

5. The chimeric receptor of claim 4, wherein cytokine receptor B-R is selected from the group consisting of an interleukin-2 receptor (IL-2R), an interleukin-3 receptor (IL-3R), an interleukin-4 receptor (IL4R), an interleukin-5 receptor (IL-5R), an interleukin6 receptor (IL-6R), an interleukin-7 receptor (IL-7R), a γ-interferon receptor (IFNγ-R) and a granulocyte/macrophage colony stimulating factor receptor (GM-CSF-R).

6. The chimeric receptor of claim 4, wherein the extracellular domains of the first and second peptide chains are derived from a first hetero-oligomeric type cytokine receptor, and herein the cytoplasmic domains of the first and second peptide chains are derived from a second hetero-oligomeric type cytokine receptor.

7. The chimeric receptor of claim 6, wherein the cytoplasmic domains of the first and second peptide chains are derived from an interleukin-2 receptor (IL-2R).

8. The chimeric receptor of claim 7, wherein the extracellular domains of the first and second peptide chains are derived from a cytokine receptor selected from the group consisting of a granulocyte/macrophage colony stimulating factor receptor (GM-CSF-R), a γ-interferon receptor (IFNγ-R), an interleukin-3 receptor (IL-3R), an interleukin-4 receptor (IL-4R) and an interleukin-7 receptor (IL-7R).

9. The chimeric receptor of claim 3, wherein cytokine receptor A-R is a cytokine receptor having high affinity ligand binding as a single chain or by homomultimerization.

10. The chimeric receptor of claim 9, wherein cytokine receptor A-R is selected from the group consisting of c-kit receptor (c-kit-R), tumor necrosis factor receptor (TNF-R), erythropoietin receptor (Epo-R) and granulocyte colony stimulating factor receptor (G-CSF-R).

11. The chimeric receptor of claim 3, wherein the extracellular domains of the first and second peptide chains are derived from a cytokine receptor having high affinity ligand binding as a single chain or by homomultimerization, and wherein the cytoplasmic domains of the first and second peptides are derived from a hetero-oligomeric type cytokine receptor.

12. The chimeric receptor of claim 11, wherein the cytoplasmic domains of the first and second peptides are derived from an interleukin-2 receptor (IL-2R).

13. The chimeric receptor of claim 3, wherein the lymphocyte is a CD8+ cytotoxic T lymphocyte (CTL).

14. The chimeric receptor of claim 13, wherein the CTL is normally dependent on cytokine B that is provided by helper T cells ($T_H$), and wherein the chimeric receptor expressed in said CTL lessens the growth dependency of the CTL on $T_H$ cells in the presence of cytokine A.

15. The chimeric receptor of claim 14, wherein cytokine receptor B-R is an interleukin-2 receptor (IL-2R) and cytokine B is interleukin-2 (IL-2).

16. The chimeric receptor of claim 15, wherein the cytokine receptor A-R is the c-kit receptor (c-kit-R).

17. The chimeric receptor of claim 15, wherein cytokine receptor A-R is selected from the group consisting of a granulocyte/macrophage colony stimulating factor receptor (GM-CSF-R), a γ-interferon receptor (IFNγ-R) and an interleukin-3 receptor (IL-3R).

18. The chimeric receptor of claim 17, wherein cytokine receptor A-R is a granulocyte/macrophage colony stimulating factor receptor (GM-CSF-R) and cytokine A is granulocyte/macrophage colony stimulating factor (GM-CSF).

19. The chimeric receptor of claim 17, wherein cytokine receptor A-R is a γ-interferon receptor (IFNγ-R) and cytokine A is γ-interferon (IFNγ).

20. The chimeric receptor of claim 17, wherein cytokine receptor A-R is an interleukin-3 receptor (IL-3R) and cytokine B is interleukin-3 (IL-3).

21. The chimeric receptor of claim 1, wherein both the cytoplasmic domain and the transmembrane domain are derived from cytokine receptor B-R.

22. The chimeric receptor of claim 3, wherein both the cytoplasmic domain and the transmembrane domain are derived from cytokine receptor B-R.

23. A recombinant polynucleotide comprising a region encoding a first peptide chain of a chimeric receptor comprising at least first and second peptide chains, wherein said peptide chains are different from each other and are each chimeric, each said chimeric peptide chain comprising an extracellular domain derived from cytokine receptor A-R that binds cytokine A, joined, via a transmembrane domain, to a cytoplasmic domain derived from cytokine receptor B-R that binds cytokine B, where cytokine receptor A-R and cytokine receptor B-R are different receptors and one of receptor A-R or B-R is hetero-oligomeric, wherein cytokine B is a cytokine that is normally required by a lymphocyte for growth and proliferation, and wherein the chimeric receptor expressed in said lymphocyte lessens the growth dependancy of the lymphocyte on cytokine B in the presence of cytokine A, and wherein said receptor A-R is selected from the group consisting of c-kit receptor, tumor necrosis factor receptor, erythropoietin receptor, granulocyte/macrophage colony stimulating factor receptor, and γ-interferon receptor.

24. The recombinant polynucleotide of claim 23 in the form of an expression vector.

25. A cell containing an expression vector of claim 24.

26. The cell of claim 25, wherein the cell is a CD8+ cytotoxic T lymphocyte (CTL).

27. A recombinant polynucleotide or pair of polynucleotides comprising regions encoding first and second chimeric peptide chains of a chimeric receptor, said chimeric receptor comprising at least first and second of said peptide chains, wherein said peptide chains are different from each other and are each chimeric, and wherein each said peptide chain comprises an extracellular domain derived from cytokine receptor A-R that binds cytokine A, joined, via a transmembrane domain, to a cytoplasmic domain derived from cytokine receptor B-R that binds cytokine B, where cytokine receptor A-R and cytokine receptor B-R are different receptors, wherein cytokine B is a cytokine that is normally required by a lymphocyte for growth and proliferation and wherein the chimeric receptor expressed in said lymphocyte lessens the growth dependency of the lymphocyte on cytokine B in the presence of cytokine A, and wherein one of cytokine receptor A-R or B-R is hetero-oligomeric.

28. A recombinant polynucleotide of claim 27, comprising a first region encoding said first chimeric peptide chain and a second region encoding said second chimeric peptide chain, wherein said first and second regions are located on a single polynucleotide.

29. The recombinant polynucleotide of claim 28 in the form of an expression vector.

30. A cell containing an expression vector of claim 29.

31. The cell of claim 30, wherein the cell is a CD8+ cytotoxic T lymphocyte (CTL).

32. A method of lessening the growth dependency of a cell on a cytokine, the method comprising transforming the cell with at least one recombinant polynucleotide comprising a region encoding a first chimeric peptide chain of a chimeric receptor, wherein the first chimeric peptide chain comprises an extracellular domain derived from cytokine receptor A-R that binds cytokine A, joined, via a transmembrane domain, to a cytoplasmic domain derived from cytokine receptor B-R that binds cytokine B, wherein cytokine B is a cytokine that is normally required by a lymphocyte for growth and proliferation and wherein the chimeric receptor expressed in said lymphocyte lessens the growth dependancy of the lymphocyte on cytokine B in the presence of cytokine A, wherein cytokine receptors A-R and B-R are different receptors, and wherein if cytokine receptor A-R or B-R is hetero-oligomeric then the chimeric receptor comprises at least first and second of said chimeric peptide chains and said peptide chains are different from each other, and if cytokine receptor A-R or B-R is hetero-oligomeric then said method comprises transforming said cell with a polynucleotide or pair of polynucleotides comprising regions encoding said first and second chimeric peptide chains.

33. The method of claim 32, wherein the recombinant polynucleotide is in the form of a recombinant expression vector.

34. The method of claim 33, wherein the lymphocyte is a CD8+ cytotoxic T lymphocyte (CTL).

35. The method of claim 34, wherein cytokine receptor B-R is an interleukin-2 receptor (IL-2R) and cytokine B is interleukin-2 (IL-2).

36. A lymphocyte cell produced by the method of claim 35 and progeny thereof.

37. The method of claim 35, wherein cytokine receptor A-R is selected from the group consisting of a granulocyte/macrophage colony stimulating factor receptor (GM-CSF-R), a γ-interferon receptor (IFNγ-R), and an interleukin-3 receptor (IL-3R).

38. A lymphocyte cell produced by the method of claim 37 and progeny thereof.

39. A cell and progeny thereof produced by the method of transforming a cell with at least one recombinant polynucleotide comprising a region encoding a first chimeric peptide chain of a chimeric receptor, wherein each said peptide chain comprises an extracellular domain derived from cytokine receptor A-R that binds cytokine A, joined, via a transmembrane domain, to a cytoplasmic domain derived from cytokine receptor B-R that binds cytokine B, wherein cytokine B is a cytokine that is normally required by a lymphocyte for growth and proliferation, wherein the chimeric receptor expressed in said lymphocyte lessens the growth dependency of the lymphocyte on cytokine B in the presence of cytokine A, wherein cytokine receptors A-R and B-R are different receptors, and wherein if cytokine receptor A-R or B-R is hetero-oligomeric then the chimeric receptor comprises at least first and second of said chimeric peptide chains and said peptide chains are different from each other, and if receptor A-R or B-R is hetero-oligomeric then said cell is produced by transforming the cell with one or a pair of polynucleotides comprising regions encoding said first and second chimeric peptide chains.

40. A cell of claim 39 and progeny thereof, wherein the recombinant polynucleotide is on at least one vector.

41. A cell of claim 40 and progeny thereof, wherein the cell is a lymphocyte.

42. A cell of claim 41 and progeny thereof, wherein the cell is a CD8+ cytotoxic T lymphocyte (CTL).

* * * * *